(12) United States Patent
Scholl et al.

(10) Patent No.: US 8,574,628 B2
(45) Date of Patent: Nov. 5, 2013

(54) NATURAL, MULTIPLE RELEASE AND RE-USE COMPOSITIONS

(75) Inventors: Neil T. Scholl, Neenah, WI (US); Vasily A. Topolkaraev, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/330,406

(22) Filed: Dec. 19, 2011

(65) Prior Publication Data

US 2013/0158129 A1    Jun. 20, 2013

(51) Int. Cl.
*A61K 9/14*    (2006.01)

(52) U.S. Cl.
USPC ............................ 424/484; 424/400; 424/489

(58) Field of Classification Search
USPC .......................................... 424/400, 484, 489
See application file for complete search history.

(56) References Cited

U.S. PATENT DOCUMENTS

| | | |
|---|---|---|
| 3,354,506 A | 11/1967 | Raley |
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,232,047 A | 11/1980 | Sair et al. |
| 4,652,441 A | 3/1987 | Okada et al. |
| 4,690,825 A | 9/1987 | Won |
| 4,695,450 A | 9/1987 | Bauer et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,380,530 A * | 1/1995 | Hill ................. 424/440 |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,603,971 A | 2/1997 | Porzio et al. |
| 5,665,428 A | 9/1997 | Cha et al. |
| 5,687,875 A | 11/1997 | Watts et al. |
| 5,702,717 A | 12/1997 | Cha et al. |
| 5,723,588 A | 3/1998 | Donofrio et al. |
| 5,735,588 A | 4/1998 | Dittman et al. |
| 5,785,179 A | 7/1998 | Buczwinski et al. |
| 5,871,872 A | 2/1999 | Matijevic et al. |
| 5,882,702 A | 3/1999 | Abdel-Malik et al. |
| 5,919,471 A | 7/1999 | Saferstein et al. |
| 5,928,661 A | 7/1999 | Fujita et al. |
| 5,964,351 A | 10/1999 | Zander |
| 6,030,331 A | 2/2000 | Zander |
| 6,090,925 A | 7/2000 | Woiszwillo et al. |
| 6,121,165 A | 9/2000 | Mackey et al. |
| 6,133,166 A | 10/2000 | Nissing et al. |
| 6,158,614 A | 12/2000 | Haines et al. |
| 6,238,682 B1 | 5/2001 | Klofta et al. |
| 6,269,969 B1 | 8/2001 | Huang et al. |
| 6,269,970 B1 | 8/2001 | Huang et al. |
| 6,270,878 B1 | 8/2001 | Wegele et al. |
| 6,273,359 B1 | 8/2001 | Newman et al. |
| 6,315,864 B2 | 11/2001 | Anderson et al. |
| 6,523,690 B1 | 2/2003 | Buck et al. |
| 6,568,625 B2 | 5/2003 | Faulks et al. |
| 6,589,549 B2 | 7/2003 | Shih et al. |
| 6,680,287 B2 | 1/2004 | Wisniewski et al. |
| 6,719,995 B2 | 4/2004 | Rajaiah et al. |
| 6,766,919 B2 | 7/2004 | Huang et al. |
| 6,770,433 B2 | 8/2004 | Hioki |
| 6,806,213 B2 | 10/2004 | Brooks |
| 6,806,353 B2 | 10/2004 | Zhang et al. |
| 6,824,734 B2 | 11/2004 | Boggs et al. |
| 6,989,149 B2 | 1/2006 | Glenn, Jr. et al. |
| 7,127,771 B2 | 10/2006 | McDevitt et al. |

(Continued)

FOREIGN PATENT DOCUMENTS

| EP | 0 388 718 A2 | 9/1990 |
|---|---|---|
| EP | 0 504 387 B1 | 7/1995 |

(Continued)

OTHER PUBLICATIONS

Co-pending U.S. Appl. No. 12/961,611, filed Dec. 7, 2010, by Lee et al. for "Wipe Coated with a Botanical Composition having Antimicrobial Properties."

(Continued)

Primary Examiner — Fereydoun G Sajjadi
Assistant Examiner — Danielle Sullivan
(74) Attorney, Agent, or Firm — Dority & Manning, P.A.

(57) ABSTRACT

A composition comprising a biopolymer matrix, said biopolymer matrix comprising from about 0.1% to about 40% of an essential oil, about 30% to about 95% of a biopolymer, and about 0% to about 50% of a carrier fluid wherein a limited amount of said essential oil can be released from said matrix composition when exposed to a liquid solution; and wherein an additional limited amount of said essential oil can be re-released repetitiously thereafter upon re-use with an additional exposure of a liquid solution.

14 Claims, No Drawings

(56) References Cited

U.S. PATENT DOCUMENTS

| | | |
|---|---|---|
| 7,250,152 B2 | 7/2007 | Gentile et al. |
| 7,338,927 B2 | 3/2008 | Shapiro |
| 7,462,348 B2 | 12/2008 | Gruenbacher et al. |
| 7,488,503 B1 | 2/2009 | Porzio et al. |
| 7,560,422 B2 | 7/2009 | Shapiro |
| 7,605,096 B2 | 10/2009 | Tomarchio et al. |
| 7,612,029 B2 | 11/2009 | Foland et al. |
| 7,614,812 B2 | 11/2009 | Reddy et al. |
| 7,662,409 B2 | 2/2010 | Masters |
| 7,803,413 B2 | 9/2010 | van Lengerich et al. |
| 7,803,414 B2 | 9/2010 | Van Lengerich et al. |
| 7,998,888 B2 | 8/2011 | Shi et al. |
| 2002/0160035 A1 | 10/2002 | Fotinos |
| 2003/0008008 A1* | 1/2003 | Leung et al. ............ 424/486 |
| 2003/0031722 A1 | 2/2003 | Cao et al. |
| 2003/0082219 A1 | 5/2003 | Warren et al. |
| 2003/0105207 A1 | 6/2003 | Kleyer et al. |
| 2003/0135172 A1 | 7/2003 | Whitmore et al. |
| 2003/0206942 A1 | 11/2003 | Kulkarni et al. |
| 2004/0018241 A1 | 1/2004 | Houze et al. |
| 2004/0026289 A1 | 2/2004 | Halkyard |
| 2004/0037870 A9 | 2/2004 | Fotinos |
| 2004/0043134 A1 | 3/2004 | Corriveau et al. |
| 2004/0180110 A1* | 9/2004 | Mistry ....................... 426/3 |
| 2004/0234609 A1 | 11/2004 | Collier et al. |
| 2004/0255408 A1 | 12/2004 | Norton et al. |
| 2005/0048121 A1 | 3/2005 | East et al. |
| 2005/0158369 A1 | 7/2005 | Dorschner et al. |
| 2005/0214349 A1 | 9/2005 | Nie et al. |
| 2005/0238591 A1 | 10/2005 | Sagel et al. |
| 2005/0245162 A1 | 11/2005 | McCormack et al. |
| 2006/0062832 A1 | 3/2006 | Lopes |
| 2006/0128248 A1 | 6/2006 | Ellis |
| 2007/0042182 A1 | 2/2007 | Markus et al. |
| 2007/0077281 A1 | 4/2007 | Theobald et al. |
| 2007/0224261 A1 | 9/2007 | Draper |
| 2007/0254035 A1 | 11/2007 | Hao et al. |
| 2007/0256247 A1 | 11/2007 | Privitera et al. |
| 2007/0269567 A1 | 11/2007 | McMindes et al. |
| 2008/0160084 A1 | 7/2008 | Huynh et al. |
| 2008/0200359 A1 | 8/2008 | Smets et al. |
| 2008/0207481 A1 | 8/2008 | Meine et al. |
| 2008/0221003 A1 | 9/2008 | Meine et al. |
| 2009/0087468 A1 | 4/2009 | Stephenson et al. |
| 2009/0136555 A1 | 5/2009 | Crowley et al. |
| 2009/0175806 A1 | 7/2009 | Modak et al. |
| 2009/0186096 A1 | 7/2009 | Kritzman et al. |
| 2009/0196909 A1 | 8/2009 | Cooper et al. |
| 2009/0226530 A1 | 9/2009 | Lassner et al. |
| 2009/0232905 A1 | 9/2009 | Weiss et al. |
| 2009/0286437 A1 | 11/2009 | Cunningham et al. |
| 2009/0297664 A1 | 12/2009 | Forte et al. |
| 2010/0034907 A1 | 2/2010 | Daigle et al. |
| 2010/0065445 A1 | 3/2010 | Stevenson |
| 2010/0101605 A1 | 4/2010 | Saint Victor |
| 2010/0136201 A1 | 6/2010 | Bigeard et al. |
| 2010/0144584 A1 | 6/2010 | Saint Victor |
| 2010/0159170 A1 | 6/2010 | Wang et al. |
| 2010/0234517 A1 | 9/2010 | Plantenberg et al. |
| 2010/0240724 A1 | 9/2010 | Chang et al. |
| 2010/0240799 A1 | 9/2010 | Hofmann et al. |
| 2010/0247371 A1 | 9/2010 | Farrugia et al. |
| 2010/0272831 A1 | 10/2010 | Lagaron Cabello et al. |
| 2011/0086084 A1 | 4/2011 | Koenig et al. |
| 2011/0086085 A1 | 4/2011 | Wenzel et al. |
| 2011/0150955 A1 | 6/2011 | Klingman |

FOREIGN PATENT DOCUMENTS

| | | |
|---|---|---|
| EP | 1 004 703 A1 | 5/2000 |
| EP | 1 023 863 A1 | 8/2000 |
| EP | 1 059 032 A1 | 12/2000 |
| EP | 1 059 378 A1 | 12/2000 |
| EP | 1 275 370 A1 | 1/2003 |
| EP | 1 275 371 A1 | 1/2003 |
| EP | 0 863 942 B1 | 9/2003 |
| EP | 1 624 013 A1 | 2/2006 |
| EP | 1 618 240 B1 | 8/2006 |
| EP | 1 408 926 B1 | 1/2007 |
| EP | 1 757 261 A2 | 2/2007 |
| EP | 1 867 317 A2 | 12/2007 |
| FR | 2 900 940 A1 | 11/2007 |
| GB | 2 444 112 A | 5/2008 |
| WO | WO 90/03784 A1 | 4/1990 |
| WO | WO 92/05708 A1 | 4/1992 |
| WO | WO 01/51557 A1 | 7/2001 |
| WO | WO 02/074430 A1 | 9/2002 |
| WO | WO 2006/000032 A1 | 1/2006 |
| WO | WO 2007/135273 A2 | 11/2007 |
| WO | WO 2008/030969 A2 | 3/2008 |
| WO | WO 2008/063088 A1 | 5/2008 |
| WO | WO 2008/149232 A2 | 12/2008 |
| WO | WO 2009/155115 A2 | 12/2009 |
| WO | WO 2010/022353 A1 | 2/2010 |

OTHER PUBLICATIONS

Co-pending U.S. Appl. No. 12/961,619, filed Dec. 7, 2010, by Lee et al. for "Wipe Coated with a Botanical Emulsion having Antimicrobial Properties."

Co-pending U.S. Appl. No. 12/961,625, filed Dec. 7, 2010, by Topolkaraev et al. for "Melt-Blended Protein Composition."

Co-pending U.S. Appl. No. 12/961,634, filed Dec. 7, 2010, by Topolkaraev et al. for "Protein Stabilized Antimicrobial Composition Formed by Melt Processing."

Co-pending U.S. Appl. No. 12/961,638, filed Dec. 7, 2010, by Wang et al. for "Melt Processed Antimicrobial Composition."

Co-pending U.S. Appl. No. 13/330,375, filed Dec. 19, 2011, by Topolkaraev et al. for "Natural, Multiple Use and Re-Use, User Saturated Wipes."

American Society for Testing Materials (ASTM) Designation: D 445-04, "Standard Test Method for Kinematic Viscosity of Transparent and Opaque Liquids (and the Calculation of Dynamic Viscosity)," pp. 1-10, published Jun. 2004.

American Society for Testing Materials (ASTM) Designation: D5034-95, "Standard Test Method for Breaking Strength and Elongation of Textile Fabrics (Grab Test)," pp. 674-681, published Jul. 1995.

Auvergne et al., "Reactivity of Wheat Gluten Protein During Mechanical Mixing: Radical and Nucleophilic Reactions for the Addition of Molecules on Sulfur," *Biomacromolecules*, vol. 9, No. 2, Feb. 2008, pp. 664-671.

"Chemistry of Crosslinking," Thermo Fisher Scientific Inc., printed from Internet web site "www.piercenet.com", 2010, pp. 1-8.

Camire, Mary Ellen, "Protein Functionality Modification by Extrusion Cooking," (Presented at the 81st AOCS Annual Meeting, Baltimore, 1990), *JAOCS*, vol. 68, No. 3, Mar. 1991, pp. 200-205.

Del Nobile, M.A. et al., "Active Packaging by Extrusion Processing of Recyclable and Biodegradable Polymers," *Journal of Food Engineering*, vol. 93, 2009, pp. 1-6.

Del Nobile, M.A. et al., "Antimicrobial Efficacy and Release Kinetics of Thymol from Zein Films," *Journal of Food Engineering*, vol. 89, 2008, pp. 57-63.

Haw, Philip, "The HLB System—A Time Saving Guide to Surfactant Selection," Uniqema, presentation to the Midwest chapter of the Society of Cosmetic Chemists, Mar. 9, 2004, 39 pages.

Hu, Dingfei and Joel Coats, "Evaluation of the Environmental Fate of Thymol and Phenethyl Propionate in the Laboratory," *Pest Management Science*, vol. 64, Issue 7, Jul. 2008, pp. 775-779.

Kurniawan, Lusiana et al., "Chemical Modification of Wheat Protein-Based Natural Polymers: Grafting and Cross-Linking Reactions with Poly(ethylene oxide) Diglycidyl Ether and Ethyl Diamine," *Biomacromolecules*, published by American Chemical Society, vol. 8, No. 9, Sep. 2007, pp. 2909-2915.

Lawton, J.W. et al, "High-Temperature, Short-Time Extrusion of Wheat Gluten and a Bran-Like Fraction," *Cereal Chemistry*, American Association of Cereal Chemists, Inc., vol. 62, No. 4, 1985, pp. 267-271.

(56) References Cited

OTHER PUBLICATIONS

Liu, Wanjun et al., "Modifications of Soy Protein Plastic with Functional Monomer with Reactive Extrusion," *J. Polym. Environ.*, vol. 16, No. 3, 2008, pp. 177-182.

Mastromatteo, M. et al., "Controlled Release of Thymol from Zein Based Film," *Innovative Food Science and Emerging Technologies*, vol. 10, 2009, pp. 222-227.

O'Lenick Jr., Anthony J., "Silicone Emulsions and Surfactants—A Review," *Silicone Spectator*, 2009 (originally published May 2000), pp. 1-18.

Parris, Nicholas et al., "Encapsulation of Essential Oils in Zein Nanospherical Particles," *Journal of Agricultural and Food Chemistry*, vol. 53, No. 12, Jun. 15, 2005, pp. 4788-4792.

Redl, A. et al., "Extrusion of Wheat Gluten Plasticized With Glycerol: Influence of Process Conditions on Flow Behavior, Rheological Properties, and Molecular Size Distribution," *Cereal Chemistry*, vol. 76, No. 3, May-Jun. 1999, pp. 361-370.

Sanchez-Garcia, M.D. et al., "Novel Polycaprolactone Nanocomposites Containing Thymol of Interest in Antimicrobial Film and Coating Applications," *Journal of Plastic Film & Sheeting*, vol. 24, Jul.-Oct. 2008, pp. 239-251.

Ullsten, N. Henrik et al., "Enlarged Processing Window of Plasticized Wheat Gluten Using Salicylic Acid," *Biomacromolecules*, vol. 7, No. 3, Mar. 2006, pp. 771-776.

Vaz, Claudia M. et al., "Soy Matrix Drug Delivery System Obtained by Melt-Processing Techniques," *Biomacromolecules*, vol. 4, No. 6, Nov./Dec. 2003, pp. 1520-1529.

Verbeek, Casparus J.R. and Lisa E. van den Berg, "Extrusion Processing and Properties of Protein-Based Thermoplastics," *Macromolecular Materials and Engineering*, vol. 295, 2010, pp. 10-21.

Article—Arfa et al., "Coating papers with soy protein isolates as inclusion matrix of carvacrol," *Food Research International*, vol. 40, Issue 1, Jan. 2007, pp. 22-32.

Search Report and Written Opinion for PCT/IB2012/056200 dated Feb. 28, 2013, 7 pages.

Search Report and Written Opinion for PCT/IB2012/056200 dated Feb. 28, 2013, 8 pages.

\* cited by examiner

NATURAL, MULTIPLE RELEASE AND RE-USE COMPOSITIONS

CROSS REFERENCE TO RELATED APPLICATION

This application continuation-in-part of U.S. patent application Ser. Nos. 12/961,638 and 12/961,634 filed Dec. 7, 2010, the entirety of which is incorporated by reference herein.

FIELD OF THE INVENTION

The present invention relates to the use of essential oil compositions that provide a durable formulation that can be re-activated via an aqueous solution for multiple use and re-use.

BACKGROUND OF THE INVENTION

Certain types of essential oils are known to be environmentally friendly and effective in providing a variety of benefits. The use of such oils in many commercial applications, however, has been limited due to their high volatility and instability in the presence of oxygen. Attempts to overcome this problem often involve the use of larger amounts of essential oils to prolong desired results. Unfortunately, this just leads to another problem in that simply incorporating higher concentrations of essential oils can lead to unintended and sometimes damaging results. Other attempts have involved the encapsulation of the oil component with certain types of polymers, such as proteins, in the presence of a solvent. For example, an article entitled "*Encapsulation of Essential Oils in Zein Nanospherical Particles*" (Parris, et al., *J. Agric. Food Chem.* 2005, 53, 4788-4792) broadly describes the encapsulation of thymol in zein nanospheres by mixing the oil with zein particles in the presence of a solvent (e.g., ethanol). The particles are said to be useful for oral or injectable administration of biological materials into the body. Another article entitled "*Controlled Release of Thymol from Zein Based Film*" (Mastromatteo, et al., *J. Innovative Food and Emerging Technologies* 2009, 10, 222-227) broadly describes films formed by dissolving corn zein and glycerol into ethanol, and thereafter adding thymol to form a solution. The solution is poured into a Petri dish and dried to form the film.

One problem with the techniques described above is that they generally rely on solvents (e.g., ethanol) to help dissolve the essential oil into a solution. A disadvantage of the use of solvents is that it puts a limit on what type of components may be employed in the composition. Additionally, solvent-based solutions require a substantial amount of time, energy, and materials for processing. Moreover, a portion of the essential oil may escape from the solution when the solvent is evaporated, which requires the use of a greater amount of oil than would normally be needed. Notwithstanding the above, the ability to use a "solventless" process in an oil and protein combination is complicated by the tendency of proteins to lose their flow properties when exposed to the intense shear and elevated temperature normally associated with melt processing. For example, proteins may undergo a conformational change ("denaturation") that causes disulfide bonds in the polypeptide to dissociate into sulfhydryl groups or thiyl radicals. Sulfhydryl groups form when disulfide bonds are chemically reduced. Thiyl radicals form when there is a mechanical scission of disulfide bonds. Once dissociated, however, free sulfhydryl groups randomly re-associate with other sulfhydryl groups to form new disulfide bond between polypeptides. Thiyl radicals can also randomly re-associate with other thiyl radicals to form new disulfide bonds or thiyl radicals may react with other amino acids to create new forms of cross-linking between polypeptides. Because one polypeptide contains multiple thiol groups, random cross-linking between polypeptide leads to formation of an "aggregated" polypeptide network, which is relatively brittle and leads to a loss of flow properties.

As such, a need currently exists for a solventless approach/method to create a composition that comprises the environmentally friendly benefits of an active essential oil while providing a stable composition that is able to provide continuous functional benefits to users.

SUMMARY OF THE INVENTION

The present invention relates to a composition comprising a biopolymer matrix, said biopolymer matrix comprising from about 0.1% to about 40% of an essential oil, about 30% to about 95% of a biopolymer, and about 0% to about 50% of a carrier fluid wherein a limited amount of said essential oil can be released from said matrix composition when exposed to a liquid solution; and wherein an additional limited amount of said essential oil can be re-released repetitiously thereafter upon re-use with an additional exposure of a liquid solution.

DETAILED DESCRIPTION OF THE INVENTION

While the specification concludes with the claims particularly pointing out and distinctly claiming the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, "essential oils" includes the term "botanical oils" and refers to a hydrophobic liquid that is extracted from herbs, flowers, trees, and other plants. They are typically present as tiny droplets between the cells of the plants and may be extracted by methods known to those of skill in the art (e.g., steam distillation, enfleurage (i.e., extraction using fat(s)), maceration, solvent extraction, or mechanical pressing). The essential oil of the present invention may be exact, isolated, purified or synthetically derived.

Generally speaking, the present invention is directed to an environmentally friendly and effective composition wherein a functional volatile, for example, an essential oil is comprised within a biopolymer. The biopolymer serves as a matrix such that the oil is able to be released in a limited amount when exposed to a liquid solution. When released, the essential oil is able to function as an active agent that provides desired benefits unique to the oil. The composition is also typically anhydrous and generally free of solvents. In this manner, the biopolymer will not generally disperse before use and prematurely release and exhaust the full amount of essential oil at one time. Instead, the biopolymer serves as matrix to disperse only a limited amount of oil upon contact with a liquid solution such as water. Due to the limited dispersion of oil, the composition can be re-activated upon repeated, re-use and exposure to the liquid solution. The composition is able to actively provide benefits over a prolonged period without the need to add more oils as an active for continuous and repeated use and re-use. In other words, the composition can be used at one point of time, allowed to dry and through simple re-exposure to an aqueous solution such as water, the same composition will be re-activated for re-use. This can be repeated a number of times before the original composition is no longer capable of activity. There would be no need to re-apply the composition itself. The only thing that is needed in this example would be to add water for re-activation of the active oil. The composition may be used alone or may be incorporated into a substrate for use within a wipe for use and repeated re-use.

I. Composition

A. Functional Volatiles

Functional volatiles are employed in the composition of the present invention as actives to deliver desirable benefits. Functional volatiles can be defined as actives that provide benefit to consumers/users, including, but not limited to antimicrobial, fragrance, skin health, odor masking, soothing, aroma therapy, topical treatments, topical cooling effect, insect repellent, respiratory health, neural stimulation and other benefits. The functional volatile of the present invention may be an oil such as an essential oil that is extracted from a plant or may be non-plant derived, such as esters, fatty acids, higher alcohols, lactones, sulfurs, terpenes, and the like. Likewise, the essential oil of the present invention may also be isolated or purified from an essential oil, or it may simply be made synthetically to mimic a compound derived from a plant. Essential oils are generally soluble in lipids and are able to impart beneficial properties that are not only advantageous but are more environmentally friendly than other active compounds. For example, some essential oils are believed to exhibit antimicrobial efficacy due to their ability to cause damage to the lipid component of the cell membrane in microorganisms inhibiting their proliferation. Other benefits may also include topical cooling treatments, skin health, analgesic properties, aroma therapeutics, odor masking, reduce skin barrier function that allows for other actives to permeate through the skin (topical drug delivery), insect repellent, and the like. Additionally, one or more oils can be utilized as the active within the composition. Examples of suitable essential oils for use in the present invention may include, for instance, anise oil, lemon oil, orange oil, oregano oil, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, Hydastis carradensis oil, Berberidaceae daceae oil, Ratanhiae and *Curcuma longa* oil, sesame oil, *macadamia* nut oil, evening primrose oil, Spanish sage oil, Spanish rosemary oil, coriander oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, $10^{th}$ and $12^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to species *Nepetcemosa* (catmint), *Nepeta citriodora*, *Nepeta elliptica*, *Nepeta hindostoma*, *Nepeta lanceolata*, *Nepeta leucophylla*, *Nepeta longiobracteata*, *Nepeta mussinii*, *Nepeta nepetella*, *Nepeta sibthorpii*, *Nepeta subsessilis*, *Nepeta tuberosa*, *Thymus glandulosus*, *Thymus hyemalis*, *Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Suitable monoterpene phenols may include, for instance, thymol, carvacrol, eucalyptol, and the like. Thymol (isopropyl-cresol) is one particularly suitable monoterpene phenol, which is a crystalline substance that has a boiling point of about 238° C. at atmospheric pressure. Carvacrol (isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils comprising monoterpene phenols as major constituents may be employed, with the final concentrations of the monoterpene phenols being within the ranges provided herein. The term "major constituent" generally refers to those essential oils having monoterpene phenols in an amount of more than about 50 wt. %. It is well-known in the art that such essential oils may also contain lesser amounts of other constituents, such as non-aromatic terpene compounds. Essential oils with organic phenolic compounds as major constituents may include, but are not limited to, anise oil, bay oil terpineless, clove bud, clove leaf, clove oil, clove stem, *origanum* oil, Peru balsam, pimento oil, eucalyptus oil, thyme oil and mixtures thereof.

Compositions of the present invention may employ essential oils in an amount of from about 0.1 wt. % to about 40 wt. %, in some embodiments from about 0.5 wt. % to about 30 wt. %, and in some embodiments, from about 1 wt. % to about 15 wt. %.

Other functional volatiles suitable for the present invention include, but are not limited to, non-plant based volatile compounds which including, but not limited to higher alcohols, terpenes, fatty acids, sulfur containing compounds, lactones, esters, and combinations thereof.

B. Biopolymer

The composition of the present invention also comprises a biopolymer. Because essential oils are unstable, the biopolymer serves as a matrix that helps to limit the amount of oil that is released for activity. Additionally, the essential oil is inherently limited in its solubility in certain liquid solutions. The essential oil is particularly limited in its solubility in water.

When a liquid solution is applied to the matrix, a limited or controlled amount of oil may be released from the matrix through various mechanisms.

First, the oil may be released from the matrix into the liquid solution via diffusion. In this case, the oil diffuses until the solubility limit of the oil is reached. The release or diffusion of the active from the matrix to the liquid solution is halted at the solubility limit and the remaining active oil ingredient stays entrapped within the biopolymer matrix until the time of re-use. Upon re-use, a new liquid solution can then be re-applied allowing for an additional limited amount of remaining active compound to be released again from the biopolymer matrix into solution. This process can be repeated multiple times allowing for multiple releases of actives from the biopolymer matrix. Through this mechanism, it is known that a limited amount is release because not the entire biopolymer matrix disperses or dissolve in the added liquid. When the biopolymer and active are extruded, an agglomerated/compacted composition is formed. Thus when liquid is added to the material it will not completely dispersion or dissolve right away. The amount of biopolymer that dissolves or disperses from the matrix is dependent on time. The amount of time needed for dispersal of such polymers so that they release the desired benefits of the active will depend at least in part upon the particular end-use design criteria. In most embodiments, the matrix will begin to disperse and release the essential oil active generally within about 5 minutes, within about 1 minute, within about 30 seconds, or within about 10 seconds.

Another mechanism that allows multiple release of active is by dispersing or dissolving the outer biopolymer matrix. When the liquid solution comes into contact with the biopolymer matrix, the biopolymer at the surface can dissolve or disperse into solution. As this dispersion or dissolving occurs, the active component is simultaneously released into the liquid solution as well. The active is release into solution because it is homogeneously mixed within the biopolymer matrix. So as the biopolymer matrix disperses or dissolves into solution so does the active component. To help control the amount of active that is released during the initial liquid solution contact, the dispersability or solubility of biopolymer within the liquid solution may be changed so that as the biopolymer becomes more dispersible or soluble in the liquid solution, larger amounts of biopolymer will disperse or dissolve in the liquid which, allows for a greater amount of active to be released. Alternatively, as the biopolymer becomes less dispersible or soluble in the liquid solution, less active is released. The biopolymer can also act as an emulsifier which facilitates concentrations of the active in the liquid solution above the active's solubility limit. The biopolymer does so by interacting its hydrophilic component with the hydrophilic solution, while interacting its hydrophobic component with the hydrophobic essential oil. For example, when proteins are used as the biopolymer, the hydrophilic based amino acid side chains interact with hydrophilic liquid, while the hydrophobic amino acid side chains interact with hydrophobic functional volatile.

Material surface area to volume ratio can also be utilized to control the multiple release of actives from the composition matrix. The greater the surface area, the greater the contact area is for the liquid solution. This greater amount of contact surface area allows for more actives to be released or biopolymer to disperse or dissolve into the liquid solution. In reverse, as surface area decreases to volume, the amount of contact area between particles and liquid decreases thereby decreasing the amount of active release and/or biopolymer dispersed. Surface area to volume ratio, thus, can be utilized to control the amount and number of time an active can be released. The biopolymer matrix can be in a variety of forms including, but not limited to, nonwoven webs, pellets, films, fibers, molded parts (such as injection molding and the like), particles/powders. Biopolymers suitable for the present invention include, but are not limited to, proteins, starches, cellulose, and combinations thereof. Biopolymers can be utilized in their native state or may be modified for particular applications.

Chemical modifications can be utilized to control the dispersability or solubility of the biopolymer within the application liquid. This indirect modification allows controlling the release amount of the active. In addition, such modifications can include cross-linking.

a. Proteins

Proteins used as biopolymers of the present invention include, but are not limited to, vegetable proteins, dairy proteins, animal proteins, as well as concentrates or isolates thereof. The protein source may be, for instance, milk (e.g., casein or caeseinates), whey, corn (e.g., zein), wheat (e.g., wheat gluten), soy, or other vegetable or animal sources. Plant proteins are particularly suitable for use in the present invention, such as zein, corn gluten, wheat gluten, whey protein, soy protein, etc. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PRO-FAM®, which typically have a protein content of 90 wt. % or more. Other purified soy protein products are also available from DuPont of Louisville, Ky. under the designation PRO—COTE® and from Central Soya under the designation Promie R.

If desired, the protein may also be modified using techniques known in the art to improve its ability to disperse in an aqueous solution, which may be applied to the composition to release the essential oil during and/or just prior to use as described in more detail below. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together such that they resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired. When employed, the pH modifier may be present in an amount such that the pH of the protein is from about 7 to about 14, and in some embodiments, from about 8 to about 12.

Hydrolysis of the protein material may also improve water solubility, and can be affected by treating the protein with a hydrolytic enzyme. Many enzymes are known in the art which hydrolyze protein materials, including, but not limited to, proteases, pectinases, lactases, and chymotrypsin. Enzyme hydrolysis is affected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

The composition of the present invention typically employs proteins in an amount of from about 30 wt. % to about 95 wt. %, in some embodiments from about 40 wt. % to about 90 wt. %, and in some embodiments, from about 50 wt. % to about 80 wt. %.

b. Starches or Carbohydrates

The biopolymer utilized in the present invention can also contain a modified starch. Because the essential oil tends to leach out during storage and before it is used in the desired application, the modified starch polymer helps enhance the long term stability of the oil and, in turn, the efficacy of the desired benefits thereof. Without intending to be limited by theory, it is believed that the physical structure of the starch can effectively encapsulate the essential oil and inhibit/control its premature release. Nevertheless, when it is desired to release the essential oil prior to and/or during use, the modified starch can disperse (e.g., disintegrate, dissolve, change physical form, etc.) when placed in an aqueous environment as described above.

Although starch polymers are produced in many plants, typical sources includes seeds of cereal grains, such as corn, waxy corn, wheat, sorghum, rice, and waxy rice; tubers, such as potatoes; roots, such as tapioca (i.e., cassaya and manioc), sweet potato, and arrowroot; and the pith of the sago palm. Regardless of its source, the starch is modified so that it possesses a higher degree of water sensitivity, which helps facilitate degradation upon contact with water. Such modified starches may be obtained through typical processes known in the art (e.g., esterification, etherification, oxidation, acid hydrolysis, enzymatic hydrolysis, and the like.). In another embodiment, the starch is modified so that it possesses a low degree of water sensitivity, which helps facilitate a lower degree of essential oil release.

Starch ethers and/or esters are particularly desirable, such as hydroxyalkyl starches. Without intending to be limited by theory, it is believed that such modified starches possess polar groups (e.g., hydroxy) and nonpolar groups (e.g., alkyl) that are capable of interacting with the polar (e.g., phenolic hydroxyl) and nonpolar (e.g., isopropyl) groups, respectively, found in monoterpene phenolic botanical oils. This enhances the ability of the starch polymer to trap and hold the botanical oil prior to use. Furthermore, the modification of the starch polymer provides enhanced chain flexibility, which even further enhances its trapping efficiency. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch. Other types of modified starches can be employed in the present invention that is known the art, such as cationic, anionic, crosslinked, oxidized, and enzyme-catalyzed.

The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylose starches are those having a number average molecular weight ("Mn") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("Mw") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("Mw/Mn"), i.e., the "polydispersity index", is also relatively high. For example, the polydispersity index may range from about 10 to about 100, and in some embodiments, from about 20 to about 80. The weight and number average molecular weights may be determined by methods known to those skilled in the art.

The composition of the present invention typically employs modified starch polymers in an amount of from about 30 wt. % to about 95 wt. %, in some embodiments from about 40 wt. % to about 90 wt. %, and in some embodiments, from about 50 wt. % to about 80 wt. %.

C. Carrier Fluid

A carrier fluid may also be employed in the composition of the present invention to help render the protein and/or starch more flowable under melt processing conditions and allow it to receive the essential oil within its internal structure. Suitable carrier fluids may include, but are not limited to, polyhydric alcohols, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), and the like. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Additionally phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters may be used. Aliphatic carboxylic acids may also be used, such as lactic acid, maleic acid, acrylic acid, copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight carrier fluid is preferred, such as those that are less than about 20,000 g/mol, less than about 5,000 g/mol or less than about 1,000 g/mol.

If desired, the carrier fluid may be selected to have a certain pH (refers to the pH prior to incorporation into the composition). For example, carrier fluids having a relatively low pH can reduce the tendency of gluten proteins to aggregate during melt processing. Thus, when gluten proteins are employed, a carrier fluid may be selected that has a pH of about 6 or less, in some embodiments from about 1 to about 5, and in some embodiments, from about 2 to about 4. Examples of such carrier fluids may include, but are not limited to, aliphatic carboxylic acids, such as lactic acid, maleic acid, acrylic acid, and the like. In other embodiments, it may be desirable to use carrier fluids having a higher pH, such as when the plant protein is not generally sensitive to pH. For example, soy proteins generally lack the cysteine residues that lead to aggregation in gluten proteins. Thus, when employed, the soy protein may be used with carrier fluids having a relatively wide range of pH levels. One example of such a carrier fluid is glycerol, which has a pH of about 6.

The amount of the carrier fluids employed depends in part on the nature of the selected essential oil and protein and may or may not be employed within the present invention. Carrier fluids are included at levels of from about 0%, or from about 5% or from about 10% to about 50%, or to about 30%, or to about 20%, by weight of the composition.

D. Other Components

Additives may be incorporated into the composition by adding them to the active oil particles. Additives function to control the multiple release mechanism of the present invention. These additives could also facilitate concentrations of active into solution above its solubility limit. Such an example includes incorporating surfactants into the particle to help release the active into the liquid solution above its solubility limit. If the active is hydrophobic and the liquid solution is hydrophilic, then addition of an additive such as a surfactant or combination thereof could help facilitate the release of the hydrophobic active in the hydrophilic liquid. Other additives or components include pigments, inorganic fillers, and processing aides.

II. Processing

The natural, biopolymer and essential oil compositions that have the capability to release actives multiple times are created via melt processing. The active is melt incorporated into the biopolymer matrix via extrusion or other melt processes. The resulting extruded strand is downsized to a particle size of choice. Particle sizes may be from about 1 micrometers to about 10000 micrometers, from about 30 micrometers to about 2000 micrometers, or from about 100 micrometers to 500 micro meters. The downsized particles can then be applied to a substrate such as a nonwoven material to create a semi-durable use wipe that disperses the desired benefit of the active oil. Other means to apply the melt process material could also be applied to this invention, which may include forming fibers or films and applying these fibers or films to nonwoven materials.

Downsizing of the extruded material can be carried out through known techniques in the art. Such downsizing methods/equipment includes but is not limited to micro pelletization, disk milling, attrition milling, granulators, grinders, rotary cutters, shredders, cryogenic grinders, solid-state shear pulverization, hammermills, impact mills, ball mills, and the like.

Despite the problems normally associated with melt processing proteins, the present inventors have discovered that the processing conditions and components may be selectively controlled to allow for the formation of a stable, melt-processed composition that is able to exhibit good mechanical properties. For example, the extrusion temperature(s) and shear rate employed during melt blending are relatively low to help limit polypeptide dissociation, thereby minimizing the impact of aggregation and embrittlement. While the use of such low temperature/shear conditions often tend to reduce mixing efficiency, the carrier fluid of the present invention may be employed to enhance the ability of the essential oil to flow into the internal structure of the protein where it can be retained until activated for release.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Example 1

The natural volatile active thymol was melt incorporated into protein and downsized, resulting in a particle capable of the multiple release of thymol with the addition and removal of water.

Materials: Wheat Gluten called WhetPro 75 from ADM, thymol from Sigma-Aldrich

Extrusion: A "PRISM USALAB 16" lab scale twin screw extruder was employed to melt process WhetPro® 75 Gluten and thymol. The extruder contained eleven (11) different zones, although zones 1 through 5, and 11 were not utilized in this Example. The extruder used a 0.75-inch die system (zone 11) to allow for ease of material to exit extruder. The protein and thymol were pre-blended (17 wt % thymol and 83% protein) and subsequently added to the extruder at zone 6 at a feed rate of 0.5 lbs/hr to give a composition of 83% WhetPro® and 17% thymol. The screw configuration was composed of conveying elements at zones 6 and 7, kneading blocks at zones 8 and 9, and conveying elements at zone 10. The screw speed was 50 rpm. The temperature profile for zones 6-11 was 37° C., 47° C., 60° C., 70° C., 70° C., and 70° C., respectively. The resulting extruded material was contained in plastic bag and stored at −32° C. Cooled material was downsized via Brickmann/Retsch lab scale grinding mill (set speed=1) and collected at a particle size <250 μm.

Multiple Wettings: To demonstrate that particle can release thymol multiple times, 1.17 grams of particles placed into 26 ml vial. 20 ml of DI water was added, waited 3 minutes, removed water from particles, repeat addition and remove of water 2 more times. Each solution was analyzed for % thymol content through high performance liquid chromatography (HPLC) analysis. Results are set forth in the table below and demonstrated that thymol is released multiple times with the addition and removal of water.

TABLE 1

Utilizing water to multiple trigger release thymol from gluten particle

| | % thymol in solution (w/w) |
|---|---|
| First wetting | 0.078 |
| Second wetting | 0.055 |
| Third wetting | 0.047 |

Example 2

Other types of liquid solutions are capable of releasing thymol multiple times from a wheat gluten matrix. Liquid solution for this example is ethanol which readily solubilizes thymol. This example demonstrates that the gluten matrix (biopolymer) controls the release of thymol from particles. If thymol was not incorporated into the gluten matrix, ethanol would completely dissolve thymol thus not allowing multiple releases. To demonstrate this, the particle was prepared as shown in Example 1. Ethanol was utilized instead of DI water. The results are set forth in the table below.

TABLE 2

Utilizing ethanol to multiple trigger release thymol from gluten particle

| | % thymol in solution (w/w) |
|---|---|
| First wetting | 0.188 |
| Second wetting | 0.336 |
| Third wetting | 0.115 |

Example 3

A wipe that releases thymol multiple times with addition and removal of water is provided. A "PRISM USALAB 16" lab scale twin screw extruder was employed to melt process WhetPro® 75 vital wheat gluten from Archer Daniels Midland, Emery 917 Glycerin 99.7% USP, Kosher from Emery Oleochemicals LLC, and thymol ≥99. % from Sigma-Aldrich. The extruder contained eleven (11) different zones, although zones 1 through 5, and 11 were not utilized in this Example. The extruder was used with a 0.75-inch die system (zone 11) to allow for ease of material to exit extruder. The gluten and thymol were pre-blended (83 wt % gluten and 17 wt % thymol) and subsequently added to the extruder at zone 6 at a feed rate of 0.5 lbs./hr. Glycerine was then added at zone 7 at a feed rate of 0.087 lbs./hr. to give an approximate composition of 71% WhetPro®, 14% glycerol, 15% thymol. The screw configuration was composed of conveying elements at zones 6 and 7, kneading blocks at zones 8 and 9, and conveying elements at zone 10. The screw speed was 50 rpm. The temperature profile for zones 9-11 was 70° C. The resulting material was contained in plastic bag and stored at −32° C. Cooled material was downsized via Brickmann/Retsch lab scale grinding mill (set speed=1). Particles less than 425 μm were removed by sieving. The ≥425 μm particles were secured between two 6 inch by 6 inch Wypall® Hydroknit X60® sheets via ultrasonic bonding. Loading level of the particles was 50 wt. % to the weight of the two 6 inch by 6 inch Wypall® Hydroknit X60® sheets. Deionized water (DI water) was added at 375 wt. % to the weight of the particle containing wipe, waited 5 minutes before expressing solution into glass vial. Wet wipe was allowed to dry for approximately 60 minutes. Added 375 wt. %, waited 5 minutes, expressed and dried for 60 minutes were repeated to collect a total of 5 expression samples from one wipe. Thymol in expression was quantified via high performance liquid chromatography. Results are set forth in Table 3.

TABLE 3

Multiple Releases of Thymol from Gluten containing Wipe

| Expression | Thymol wt. % in Expression Solution |
|---|---|
| 1st Expression | 0.021 |
| 2nd Expression | 0.017 |
| 3rd Expression | 0.018 |
| 4th Expression | 0.016 |
| 5th Expression | 0.017 |

Example 4

A wipe that release thymol multiple times with the addition and removal of water is demonstrated. Hydroxypropyl starch phosphate called Structure® XL from Akzo Nobel, Emery 917 Glycerin 99.7% USP, Kosher from Emery Oleochemicals LLC, and thymol ≥99. % from Sigma-Aldrich were blended together via Kitchen Aide mixer at percentages of 80 wt. %, 15 wt. %, and 5 wt. % respectively. The resulting blend was starve fed into zone 1 of "PRISM USALAB 16" lab scale twin screw extruder at a feed rate of 0.75 lbs./hr. Temperature profile for zones 2-11 were 85° C., 95° C., 102° C., 115° C., 128° C., 123° C., 117° C., 114° C., 104° C., 96° C. respectively. Screw speed was 200 rpm. Temperature zone 11 was 3 mm strand die. The extruded strand was pelletized, and downsized via Brickmann/Retch lab scale grinding mill (set speed=1) and sieved to collect particles with size range from 250-425 μm. The resulting particles were secured between two 6 inch by 6 inch Wypall® Hydroknit X60® sheets via ultrasonic bonding. Loading level of the particles were 50 wt. % to the weight of the two 6 inch by 6 inch Wypall® Hydroknit X60® sheets. Deionized water (DI water) was added at 375 wt. % to the weight of the particle containing wipe, waited 5 minutes before expressing solution into a glass vial. Wet wipe was allowed to dry for approximately 60 minutes. Adding 375 wt. %, waiting 5 minutes, expressed and dried for 60 minutes were repeated to collect a total of 5 expression samples from one wipe. Thymol in expression solution was quantified via high performance liquid chromatography. Results are set forth in Table 4.

TABLE 4

Multiple Releases of Thymol from Starch containing Wipe

| Expression | Thymol wt. % in Expression Solution |
|---|---|
| 1st Expression | 0.151 |
| 2nd Expression | 0.040 |
| 3rd Expression | 0.026 |
| 4th Expression | 0.004 |
| 5th Expression | 0.004 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising a biopolymer matrix, said biopolymer matrix comprising from about 0.1% to about 40% of an essential oil based on the total weight of the composition, about 30% to about 95% of a biopolymer based on the total weight of the composition, and about 5% to about 50% of a carrier fluid based on the total weight of the composition; wherein a portion of the about 0.1% to about 40% of the essential oil can be released from said matrix composition when exposed to a liquid solution; and wherein an additional portion of the about 0.1% to about 40% of the essential oil can be re-released repetitiously thereafter upon removal of liquid followed by additional exposure of a liquid solution, wherein the biopolymer matrix is in the form of particles having a particle size of from about 1 micrometer to about 10,000 micrometers, wherein the particles are formed by downsizing an extruded strand of the biopolymer matrix.

2. The composition of claim 1 wherein the essential oil comprises a monoterpene phenol selected from thymol, carvacrol, and mixtures thereof.

3. The composition of claim 2 wherein the monoterpene phenol is thymol.

4. The composition of claim 1 wherein the biopolymer is selected from proteins, starches, cellulose, and mixtures thereof.

5. The composition of claim 4 wherein the protein is selected from soy, wheat gluten, and mixtures thereof.

6. The composition of claim 5 wherein the protein is wheat gluten.

7. The composition of claim 1 wherein the carrier fluid is selected from polyhydric alcohols, aliphatic carboxylic acids, and mixtures thereof.

8. The composition of claim 1 wherein the carrier fluid has a molecular weight less than about 20,000 g/mol.

9. The composition of claim 8 wherein the carrier fluid has a pH of about 6 or less.

10. The composition of claim 5 wherein the protein is soy protein.

11. The composition of claim 9 wherein the carrier fluid is glycerol with a pH of about 6.

12. The composition of claim 1 wherein the essential oil is released in a controlled amount through mechanisms selected from interaction with the liquid solution, dissolution of the biopolymer matrix, adjusting the surface area to volume ratio, and combinations thereof.

13. The composition of claim 1, said biopolymer matrix comprising from 5% to about 15% of an essential oil based on the total weight of the composition.

14. A wipe comprising the composition of claim 1.

* * * * *